(12) United States Patent
Chen et al.

(10) Patent No.: US 6,555,558 B2
(45) Date of Patent: Apr. 29, 2003

(54) ORAL DOSAGE SELF-EMULSIFYING FORMULATIONS OF PYRANONE PROTEASE INHIBITORS

(75) Inventors: Shirlynn Chen, Somers, NY (US); Jocelyn A. Gunn, Hamden, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/020,492

(22) Filed: Oct. 30, 2001

(65) Prior Publication Data

US 2002/0115690 A1 Aug. 22, 2002

Related U.S. Application Data

(60) Provisional application No. 60/244,434, filed on Oct. 31, 2000.

(51) Int. Cl.[7] ............................................. A61K 31/44
(52) U.S. Cl. ........................ 514/336; 514/459; 514/460; 424/455
(58) Field of Search ................................. 424/451, 455, 424/456; 514/459, 460, 557, 558, 560, 336

(56) References Cited

U.S. PATENT DOCUMENTS

| 5,484,801 | A | * | 1/1996 | Al-Razzak et al. | 514/365 |
|---|---|---|---|---|---|
| 6,008,228 | A | * | 12/1999 | Bailey et al. | 514/307 |
| 6,121,313 | A | * | 9/2000 | Gao et al. | 514/459 |
| 6,147,095 | A | * | 11/2000 | Ferry et al. | 514/336 |
| 6,231,887 | B1 | * | 5/2001 | Gao et al. | 424/451 |

* cited by examiner

*Primary Examiner*—James H. Reamer
(74) *Attorney, Agent, or Firm*—Robert P. Raymond; Alan R. Stempel; Mary-Ellen M. Devlin

(57) ABSTRACT

A microemulsion of pyranone protease inhibitor compounds that is substantially free of alcohol and propylene glycol comprising a pyranone protease inhibitor, one or more pharmaceutically acceptable surfactants, and a polyethylene glycol solvent having a mean molecular weight of greater than 300 but lower than 600, and a lipophilic component comprising medium chain mono- and di-glycerides, and optionally a basic amine.

37 Claims, 7 Drawing Sheets

ORAL DOSAGE SELF-EMULSIFYING FORMULATIONS OF PYRANONE PROTEASE INHIBITORS

This application is a continuation-in-part of prior provisional application U.S. Ser. No. 60/244,434 filed Oct. 31, 2000.

BACKGROUND OF THE INVENTION

1. Field of the Invention

The present invention relates to unique oral dosage formulations of 5,6-dihydro-4-hydroxy-2-pyrones compounds. In particular, the present invention relates to a substantially alcohol-free and propylene glycol-free, microemulsion formulation of 5,6-dihydro-4-hydroxy-2-pyrone protease inhibitors, which formulation substantially improves bioavailability and stability at room temperature.

2. Background of the Related Art

Since the identification of acquired immunodeficiency syndrome (AIDS) in the early 1980s, AIDS and its devastating consequences have become a subject of intense coverage in the press and study in the scientific literature. It is widely held that such syndrome is due to infection with a retrovirus commonly referred to as the human immunodeficiency virus (HIV). From its identification nearly twenty years ago until today, AIDS has progressed from a medical curiosity affecting only a small population to a problem of major proportion. Millions of people in the United States alone are believed to be seropositive for HIV.

The first drug approved for the treatment of HIV infected individuals was zidovudine (AZT) on Mar. 20, 1987. Zidovudine or AZT was approved to treat AIDS patients with recent initial episodes of pneumocystis carinii pneumonia, carinii pneumonia or patients infected with the virus and having an absolute CD4 lymphocyte count of less than 200/mm$^3$ in the peripheral blood. AZT is believed to work by inhibiting viral reverse transcriptase, an enzyme necessary for human immunodeficiency virus replication.

In a very short period of time, the number of approved anti-retroviral drugs has increased from one drug with modest activity to twelve with substantial potency. The approved anti-retroviral drugs represent three classes: the nucleoside analog reverse transcriptase inhibitors; the non-nucleoside analog reverse transcriptase inhibitors; and the protease inhibitors. Highly active anti-retroviral therapy (known as "HAART") almost invariably includes a protease inhibitor in combination with one or more drugs from the other classes. Protease inhibitors as a class demonstrate potent anti-retroviral activity.

The first protease inhibitor was approved by the U.S. Food and Drug Administration ("U.S. FDA") in 1995, and such class of drugs can be said to have revolutionized the treatment of HIV infection. The protease inhibitors may be characterized as having converted what was once considered to be a uniformly fatal disease to a more treatable, chronic infectious disease. Presently there are five protease inhibitors approved by the U.S. FDA: amprenavir, indinavir, nelfinavir, ritonavir and saquinavir.

Retroviral proteases are enzymes essential for maturation of viral particles to their infectious stages. Inhibition of the proteases, or their absence or non-functionality, results in the virus being unable to efficiently replicate, thereby preventing the production of infective viral particles. For example, the retroviral protease "gag-protease," one of the smallest enzymes yet characterized (consisting of only 99 amino acids and demonstrating homology to aspartyl proteases such as pepsin and renin) is responsible for the correct proteolytic cleavage of the precursor proteins that are produced from the genome regions coding for the "group specific antigens" ("gag"). The protease is believed to be encoded by the "pol" region of the viral genome, which also contains regions for reverse transcriptase and integrase. Gag-protease cleaves the major core protein p24 of HIV-1 and HIV-2 preferentially N-terminally of proline residues; for example, in the divalent residues Phe-pro, Leu-Pro or Tyr-Pro. During cleavage, the structural proteins of the virus core are liberated. In sum, gag-protease is needed for processing HIV-fusion polypeptide precursors permitting maturation of the gag and gag/pol fusion polypeptides, including capsid and replicative enzymes (e.g., reverse transcriptase, integrase).

A number of highly potent HIV protease inhibitors have been described in the literature. By protease inhibitors it is meant a group of compounds that inhibit aspartate proteases of viral origin and which are useful in the prophylaxis or treatment of viral infections caused by retroviruses, such as HIV in mammals. Protease inhibitors can be said to have revolutionized the treatment of HIV infection in that combination therapy using such compounds with inhibitors of viral DNA polymerase reverse transcriptase can result in the apparent complete suppression of virus replication. Resistance to protease inhibitors is believed to be the result of mutations within the retroviral protease coding domain. Unfortunately, with respect to the five currently approved protease inhibitors in the United States, most of these mutations are able to contribute to cross-resistance (Swanstrom et al., Pharmacol. Ther., 86(2): 145–170 (2000)).

HIV protease inhibitors may be peptidemimetic or non-peptidemimetic in nature.

Compounds of a reduced peptidic nature, or non-peptidic nature, generally show improved pharmacokinetic profiles over their peptidic counterparts. Peptidic HIV protease inhibitors frequently demonstrate low bioavailability and rapid excretion owing to rapid gastrointestinal breakdown. In general, non-peptidic compounds have better bioavailability and are not excreted as rapidly.

Presently available non-peptidic proteinase inhibitors may be characterized as hydrophobic and/or lipophilic in character. Because of such solubility characteristic, i.e., poor aqueous solubility, conventional solid and liquid pharmaceutical preparations containing these inhibitors may not be absorbed in a satisfactory manner. Of the various factors that can affect the bioavailability of a drug when administered orally (which include aqueous solubility, drug absorption through the gastrointestinal tract, dosage strength and first pass effect), aqueous solubility is often found to be among the most important factors. Poorly water soluble compounds often exhibit either erratic or incomplete absorption, and thus produce a less than desirable response.

5,6-dihydro-4-hydroxy-2-pyrone compounds are known to be potent inhibitors of retroviral proteases. They are thus useful in inhibiting the replication of the human immunodeficiency virus (strains of HIV-1 or HIV-2 and/or human T-cell leukemia viruses (HTLV-I or HTLV-II) and in preventing AIDS. Such protease inhibitors, however, generally demonstrate extremely poor aqueous solubility. For example, the free acid form of the 5,6-dihydro-4-hydroxy-2-pyrone sulfonamide compound, tipranavir, has an extremely low aqueous solubility of about 10 µg/ml at a pH of from about 6 to about 7. Nearly 15 capsules per dose, twice a day, of the disodium salt (4.5 grams) must be taken in order to achieve a therapeutic drug level. Attempts to identify other salts of such compounds in solid forms, which would substantially improve aqueous solubility, have not been successful. Formulations of salts of these compounds generally are prone to precipitation of the parent free-acid in the gastrointestinal tract.

Many attempts have been made to improve the bioavailability of non-peptidic protease inhibitors in general, and 5,6-dihydro-4-hydroxy-2-pyrone peptidase inhibitors in particular. There is an art-recognized need for developing improved oral dosage forms of HIV protease inhibitors, which will have suitable oral bioavailability, stability and side effects profiles. Given the low solubility of many non-peptidic protease inhibitors in free and salt form, a number of efforts have been undertaken to deliver the drug in so-called "emulsified" formulations, that is, formulations containing the drug, a hydrophilic phase, and a lipophilic phase. Such strategy may be borrowed from a similar strategy undertaken with respect to solubilization of cyclic poly-N-methylated undecapeptides of the cyclosporin class, the bioavailability of which were significantly improved by mixing them in an emulsion comprising a lipophilic phase of medium-chain fatty acid triglycerides, a hydrophilic surfactant such as Cremophor RH 40 (BASF Corp.), and propylene glycol (See, EP Patent No. 0 539 319 B1). So-called SEDDS (self-emulsifying drug delivery system) formulations use high lipid and surfactant content to adequately disperse the drug upon mixing with an aqueous medium.

International Application No. PCT/US97/20794 (WO 98/22106) to Abbott Laboratories discloses an oral liquid SEDDS pharmaceutical composition which is said to improve the oral bioavailability of HIV protease inhibitors, including certain protease inhibitors of the 5,6-dihydro-4-hydroxy-2-pyrone class. Such composition comprises a pharmaceutically acceptable emulsified composition comprising a long-chain fatty acid composition, or a mixture of a pharmaceutically acceptable long-chain fatty acid and a pharmaceutically acceptable alcohol, and optionally a surfactant (such as Cremophor EL, BASF Corp.). Preferred compositions comprise ethanol or propylene glycol or both. It is stated that it is preferred that the long-chain fatty acid composition comprises from about 40 to about 70 percent by weight of the total solution, the surfactant from about 5 to about 10 percent by weight of the total solution, and ethanol or propylene glycol comprises from about 1 to about 15 percent by weight of the total solution. A study in beagles and humans demonstrates that, for at least five HIV protease inhibitors, improved mean bioavailability is seen over the free base and bis-toxylate salt of the HIV protease inhibitor ritonavir.

U.S. Pat. No. 5,484,801 to Abbott Laboratories covers a pharmaceutical composition with an HIV protease inhibiting compound in a pharmaceutically acceptable organic solvent which composition has: (a) a solvent selected from propylene glycol and polyethylene glycol (in an amount of from about 10 percent to about 50 percent by weight of the total solution) or (b) a solvent selected from polyoxyethyleneglycerol, triricinoleate, polyethylene glycol 40 hydrogenated castor oil, fractionated coconut oil, polyoxyethylene sorbitan monocleate and 2-(2-ethoxyethoxy) ethanol (in an amount of from about 5 percent to about 35 percent by weight of the total solution) or (c) a mixture thereof, and ethanol or propylene glycol (in an amount of about 5 percent to about 45 percent by weight of the total solution).

International Application No. PCT/EP96/02431 (WO 96/39142) and U.S. Pat. No. 6,008,228 to F. Hoffmann-La Roche AG teach a pharmaceutical composition which is also said to improve the bioavailability of protease inhibitors. The composition includes a pharmaceutically acceptable carrier comprising monoglycerides of medium-chain fatty acids, which preferably include monoglycerides of saturated $C_6$ to $C_{12}$ fatty acids and have an acid value of less than or equal to about 2.5. It is said that it is preferred that the ratio of monoglycerides of medium chain fatty acid to the protease inhibitor be about at least 1.5.

International Patent Nos. PCT/US95/0529 to UpJohn, that discloses the usefulness of 5,6-dihydro-4-hydroxy-2-pyrone compounds to treat retroviral infections, does not recognize the inherent bioavailability problems of such compounds. The patent teaches that such compounds may be prepared in conventional compressed tablets (mixing the compounds with conventional ingredients such as talc, magnesium stearate, etc.), as disodium salts, or prepared in conventional syrups and elixirs.

International Patent Applications PCT/US98/14816 (WO 99/06043), PCT/US98/14817 (WO 99/06044), PCT/US98/14818 (WO 99/06024), and U.S. Pat. No. 6,121,313 to Pharmacia & UpJohn Company teach self-emulsifying formulations containing alkaline active compounds which are said to provide for improved oral bioavailabilty of such compounds. The patents disclose compositions including a mixture of diglyceride and monoglycerides or basic amines along with one or more pharmaceutically acceptable surfactants and solvents which are said to provide increased absolute oral bioavailabilies. A preferred surfactant is Cremophor EL or Cremophor RH40, and a preferred solvent is propylene glycol or a mixture comprising propylene glycol and 95% (v/v) ethanol.

With respect to 5,6-dihydro-4-hydroxy-2-pyrone protease inhibitors, PCT/US98/14816 teaches that the solvent used may comprise polypropylene glycol, propylene glycol, polyethylene glycol, glycerol, ethanol, triacetin, dimethyl isosorbide, glycolfurol, propylene carbonate, water, dimethyl acetamide or a mixture thereof. The preferred solvent for such compounds is said to be propylene glycol or a mixture comprising propylene glycol and 95% (v/v) ethanol. In a mixture of propylene glycol and ethanol, propylene glycol is said to be in an amount of from about 50% to about 95%. The surfactants found useful with such compounds are disclosed to be non-ionic surfactants including Polyoxyl 40 hydrogenated castor oil (e.g. Cremophor RH40), Polyoxyl 35 castor oil (eg. Cremophor EL or Cremophor EL-P), polysorbates, Solutol HS-15, Tagat TO, Peglicol 6-oleate, polyoxyethylene stearates, saturated polyglycolyzed glycerides, or poloxamers. The preferred surfactants for such emulsified compositions are specified to be Cremophor RH40 or Cremophor EL. When amines are employed in the composition it is disclosed that such should comprise lower alkylamines such as ethanolamine, diethanolamine, triethanolamine, dimethylamino-ethanol, tris (hydroxymethyl) aminomethane or ethylenediamine; quaternary ammoniums such as choline hydroxide; and basic amino acids such as arginine, lysine or guanidine. The preferred lower alkylamine is dimethylaminoethanol or tris (hydroxymethyl) aminomethane. When a mixture of diglyceride and monoglyceride is included in the composition, such mixture preferably comprises a ratio of from about 9:1 to about 6:4 by weight (diglyceride: monoglyceride) wherein the diglyceride and monoglyceride are mono- or di-unsaturated fatty acid esters of glycerol having sixteen to twenty-two carbon atom chain length. A typical pyranone composition of the invention is said to comprise from 1 to 40 percent of the drug, from about 5 to 35 percent of diglyceride and monoglyceride mixture, and from about 10 to about 50 percent by weight of the pharmaceutically acceptable solvent. A basic amine may be optionally added in an amount of from about 0.1 to about 10 percent by weight of the total composition.

Among the 5,6-dihydro-4-hydroxy-2-pyrones known to have protease inhibitory activity, the 5,6-dihydro-4-hydroxy-2-pyrone sulfonamide class has in particular been found to demonstrate high protease inhibitory activity (Turner et al., J Med. Chem., 41(3): 3467–3476 (1998)). One in particular has shown excellent potency against the viral aspartate proteases of a variety of HIV type 1 laboratory strains and clinical isolates, including those resistant to the reverse transcriptase inhibitors zidovudine and delavirdine—the non-peptide compound HIV protease inhibitor, tipranavir, (6R)-3-[{(1R)-1-[3-({[5-(trifluoromethyl)(2-pyridyl)]sulfonyl}amino)phenyl]propyl}-4hydroxy-6-(2-phenylethyl)-6-propyl-5,6-dihydro-2H-pyran-2-one (also published under the designations U-140690 and PNU-140690):

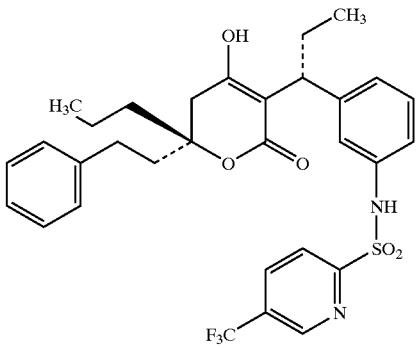

Formula IV

Tipranavir (Formula IV) (M. W.=602.98) is known to be highly active against HIV-1 variants resistant to the peptidomimetic protease inhibitors (Poppe et al., Antimicrob. Agents Chemother., 41(5): 1058–1063 (1997)). In vitro studies with the drug demonstrate a Ki value of about 8 pM (i.e., high enzymatic inhibition) and an IC90 value of about 100 nM in antiviral cell culture (Turner et al., J. Med. Chem., 41(18): 3467–3476 (1998)). It has a Log P of about 6.1, and pKas at 6.2 and 8.2. It is hypothesized that tipranavir binds in a flexible matter to the protease active site, making it a better protease inhibitor than the other presently available protease inhibitors (Larder et al., IAPAC 3rd International Workshop on HIV Drug Resistance and Treatment Strategies, Jun. 23–26 (1999)).

In an in vitro culture study of 134 clinical isolates with a wide range of resistance to currently available peptidomimetic protease inhibitors, it was determined that of 105 viruses with more than tenfold resistance to three or four proteinase inhibitors, and an average of 6.1 mutations in the protease enzyme gene, ninety percent were susceptible to tipranavir (Larder et al., AIDS, 14(13): 1943–1948 (2000)). In another study, tipranavir has been shown to retain sustained antiviral activity against isolates resistant to indinavir, ritonavir and nelfinavir, three presently available protease inhibitors (Rusconi et al., Antimicrob. Agents Chemother., 44(5): 1328–1332 (2000). Similar sustained activity has also been reported with respect to saquinavir resistance (Larder et al., IAPAC 3rd International Workshop on HIV Drug Resistance and Treatment Strategies, Jun. 23–26 (1999)).

5,6-dihydro-4-hydroxy-2-pyrone protease inhibitors, and in particular the 5,6-dihydro-4-hydroxy-2-pyrone sulfonamide inhibitors, such as tipranavir, have been found to be particularly difficult to formulate into oral dosage forms. Numerous attempts have been undertaken to formulate such drugs into a reasonably bioavailable oral product. Tipranavir, for example, forms highly hygroscopic salts, reducing the stability of the drug. The innovator of tipranavir, after numerous years of attempting to define an optimal oral formulation, currently produces an emulsified formulation comprising the drug, a lipophilic phase comprising a mixture of diglycerides and monoglycerides, a surfactant, a basic amine, and an aqueous phase comprising propylene glycol and alcohol, all packaged in a soft gelatin capsule. Such formulation while providing good oral bioavailabilty of the drug suffers from a number of drawbacks including: a tendency of the capsules to soften and to stick to one another over time; a noticeable decrease in bioavailability after encapsulation in a soft gelatin capsule; a need to refrigerate the formulation until use to prevent change in capsule composition; and the requirement of complicated manufacturing processes which must be employed to produce consistent capsule fills, especially due to the highly volatile nature of ethanol.

There is a need therefore, for improved oral formulations of protease inhibitors in general, more particularly of 5,6-dihydro-4-hydroxy-2-pyrone protease inhibitors, and yet more particularly of 5,6-dihydro-4-hydroxy-2-pyrone sulfonamide protease inhibitors such as tipranavir.

SUMMARY OF THE INVENTION

The present invention discloses improved oral formulations of pyranone protease inhibitors and processes for manufacturing such formulations. Such formulations provide for improved solubilization, stability and/or bioavailability of the pyranone drug and permit less onerous manufacturing processes to be undertaken in the fill process and allow the capsules to be stored at room temperature. In particular, advantageous oral dosage formulations of tipranavir are provided.

By "pyranone" compounds, it is meant compounds of Formula I:

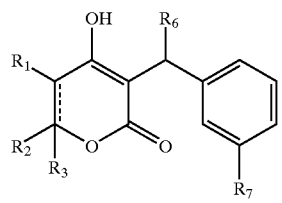

Formula I

Wherein $R_1$ is H—; $R_2$ is $C_3$–$C_5$ alkyl, phenyl-$(CH_2)_2$—, het-$SO_2$NH—$(CH_2)_2$—, cyclopropyl-$(CH_2)_2$—, F-phenyl-$(CH_2)_2$—, het-$SO_2$NH-phenyl-, or $F_3C$—$(CH_2)_2$—; or $R_1$ and $R_2$ taken together are a double bond; $R_3$ is $R_4$—$(CH_2)_n$—CH($R_5$)—, $H_3C$—[O$(CH_2)_2$]$_2$—$CH_2$—, $C_3$–$C_5$ alkyl, phenyl-$(CH_2)_2$—, het-$SO_2$NH—$(CH_2)_2$—, $(HOCH_2)_3$ C—NH—C(O)—NH—$(CH_2)_3$—, $(HO_2C)(H_2N)$CH—$(CH_2)_2$—C(O)—NH—$(CH_2)_3$—, piperazin-1-yl-C(O)—NH—$(CH_2)_3$, $HO_3S(CH_2)_2$—N$(CH_3)$—C(O)—$(CH_2)_6$—C(O)—NH—$(CH_2)_3$—, cyclopropyl-$(CH_2)_2$—, F-phenyl-$(CH_2)_2$—, het-$SO_2$ NH-phenyl, or $F_3C$—$(CH_2)_2$—; n is 0, 1 or 2; $R_4$ is phenyl, het, cycloploryl, $H_3C$—[O$(CH_2)_2$]$_2$—, het-$SO_2$NH—, Br—, $N_3$—, or $HO_3S$ $(CH_2)_2$—N$(CH_3)$—C(O)—$(CH_2)_6$—C(O)—NH—; $R_5$ is —$CH_2$—$CH_3$, or —$CH_2$-cyclopropyl; $R_6$ is cyclopropyl, $CH_3$—$CH_2$—, or t-butyl; $R_7$ is —$NR_8SO_2$-het, —$NR_8SO_2$- phenyl, optionally substituted with $R_9$, —$CH_2$—$SO_2$-phenyl, optionally substituted with $R_9$, or —$CH_2$—$SO_2$-het; $R_8$ is —H, or —$CH_3$; $R_9$ is —CN, —F, —OH, or —$NO_2$; wherein het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —C(O)O$C_2H_5$, —$CF_3$, —$NH_2$, or —C(O)—$NH_2$; or a pharmaceutically acceptable salt thereof; and

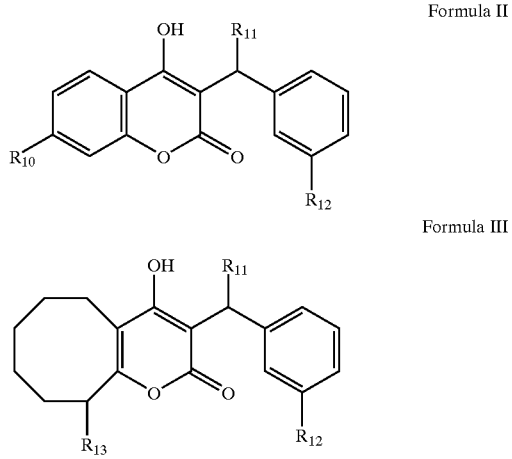

Formula II

Formula III

As Well as Compounds of Formula II and Formula III:

wherein $R_{10}$ is H—, $CH_3O$—, or $CH_3O$—[$(CH_2)_2O]_3$—; $R_{11}$ is cyclopropyl, or —$CH_2$—$CH(CH_3)_2$; $R_{12}$ is —$NR_{14}SO_2$-phenyl, optionally substituted with $R_{15}$,— $NR_{14}SO_2$-het, —$CH_2$—$SO_2$-phenyl, optionally substituted with $R_{15}$, or —$CH_2$—$SO_2$-het; $R_{13}$ is —H, —$(CH_2)_2$—$CH_3$, —$CH_2$-cyclopropyl, or —$CH_2$-phenyl; $R_{14}$ is —H, or —$CH_3$; $R_{15}$ is —CN, —F, —$CH_3$, —COOH, or —OH; het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle; optionally substituted with one or two —$CH_3$, —CN, —C(O)O$C_2H_5$, or —OH; or a pharmaceutically acceptable salt thereof.

It has been discovered that much of the difficulty with present day pyranone protease inhibitor oral formulations pertains to the use of ethanol and propylene glycol in the formulation. As discussed above with respect to prior art disclosures, while other solvents have been suggested to find utility in forming a microemulsion of pyranone protease inhibitor compounds, the incorporation of ethanol and propylene glycol into such microemulsion formulations has long been thought to be preferred and to lead to an optimal formulation. These solvents, while very good in forming emulsions of pyranone protease inhibitors, have been discovered to migrate into the gelatin shells surrounding such microemulsion formulations, thereby causing a change in the phase composition of the formulation, the solubility of the drug, and adversely affecting the structural integrity of the capsule. As a result, the capsules become sticky at room temperature and therefore require refrigerated storage condition.

Novel self-emulsifying formulations have been discovered which do not require the inclusion of ethanol or propylene glycol in the formulation. As these formulations are particularly stable at room temperature, a greatly improved pharmaceutical preparation for oral administration of pyranone protease inhibitors is disclosed. Such formulation offers patients taking pyranone protease inhibitors the ability to free their activities from places within the reach of facilities offering adequate refrigeration. Furthermore, such formulation shows a significantly more consistent bioavailability profile than present day formulations which use significant amounts of ethanol or propylene glycol in their formulations.

The present invention concerns a formulation that is substantially free of significant amounts of ethanol and propylene glycol (preferably less than about 0.5%, more preferably less than about 0.1%, alone or in combination) that provides for a significantly more stable formulation of pyranone protease inhibitors and in particular sulfonamide pyranone protease inhibitors such as tipranavir. Such formulations comprise from about 1 to about 40 percent by weight of total composition pyranone protease inhibitor, from about 5 to about 35 percent by weight of the total composition of a lipophilic phase, preferably a mixture of diglycerides and monoglycerides, from about 20 to about 60 percent by weight of the total composition surfactant, and about 10 to about 40 percent by weight of the total composition of a polyethylene glycol having an average molecular weight of greater than about 300 but less than 600, and from about 0.1 to about 10 percent by weight of the total composition of one or more basic amines.

Surprisingly, it has been determined by the present inventor that polyethylene glycols having an average molecular weight of greater than about 300 but less than 600 (preferably about 400) may be used in self-emulsifying microemulsion formulations to solubilize pyranone protease inhibitors, in particular sulfonamide pyranone protease inhibitors, without the need for alcohol or propylene glycol, and that such polymers do not migrate into or adversely affect gelatin capsules.

Presented with numerous alternative possibilities for formulating the pyranone protease inhibitors without alcohol or propylene glycol, numerous microemulsion phase studies were undertaken using various combinations of materials to determine workable formulations having clinically significant bioavailabilities. After numerous failed attempts, it was discovered that certain polyethylene glycols, of appropriate molecular weight, could effectively replace propylene glycol and/or ethanol used in conventional pyranone protease inhibitor formulations. Such alteration is relatively cheap and effective, and was surprisingly found to significantly improve the bioavailabilty and stability.

In one embodiment, there is disclosed a pharmaceutical composition substantially free of alcohol and propylene glycol comprising a pyranone compound of formula I, II or III as a pharmaceutically active agent, one or more pharmaceutically acceptable surfactants; and a polyethylene glycol having a mean molecular weight of greater than 300 but lower than 600. The pharmaceutical preferably comprises a compound of formula I, II or III in an amount from about 1% to about 40% by weight of the total composition, and further comprises a basic amine in an amount from about 0.1% to about 10% by weight of the total composition. The basic amine is preferably a lower alkylamine, basic amino acid or choline hydroxide, with the lower alkylamine preferably being selected from the group consisting of: ethanolamine, diethanolamine, triethanolamine, ethylenediamine, dimethylaminoethanol or tris(hydroxymethyl) aminomethane. The pharmaceutical composition may further comprise a mixture of monoglycerides and diglycerides in an amount from about 5% to about 35% by weight of the total composition, which preferably comprises Capmul MCM. The composition works particularly well with the tipranavir, the compound of formula IV. It is further preferred that the polyethylene glycol be in an amount from about 10% to about 40% by weight of the total composition. It is advantageously preferred that the polyethylene glycol have an average molecular weight of about 400. It is preferred that the pharmaceutically acceptable surfactant comprise from about 20% to about 60% by weight of the total composition, and that the surfactant be selected from the group consisting of: Polyoxyl 40 hydrogenated castor oil, Polyoxyl 35 castor oil, Solutol HS-15, Tagat TO, Peglicol 6-oleate, polyoxyethylene stearates, poloxamers, polysorbates, or saturated polyglycolyzed glycerides. The preferred Polyoxyl 35 hydrogenated castor oil is Cremophor EL, or Cremophor EL-P.

In another embodiment of the present invention, there is disclosed a substantially alcohol and propylene glycol free pharmaceutical composition comprising tipranavir (formula IV) in an amount from about 1% to about 40% by weight of the total composition; a lipophilic phase comprising from about 5% to about 35% by weight of the total composition; polyethylene glycol having a mean molecular weight of greater than about 300 but less than about 600 in an amount from about 10% to about 40% by weight of the total composition; a pharmaceutical acceptable surfactant, preferably selected from the group comprising: a polyoxyl castor oil, a polyoxyethylene glycerol triricinoleate, and a saturated polyglycolyzed caprylic-capric glyceride, in an amount from about 20 to about 60 percent by weight of the total composition; and a basic amine, preferably selected from the group comprising: a lower alkylamine, basic amino acid, or choline hydroxide, said basic amine in an amount from about 0.1% to about 10% by weight of the total composition. A preferred lipophilic phase comprises a mixture of medium-chain monoglycerides and diglycerides, such as Capmul MCM.

And yet in another embodiment of the present invention, there is disclosed a substantially alcohol and propylene glycol free pharmaceutical composition comprising: tipranavir (Formula IV) in an amount from about 1% to about 40% by weight of the total composition; a lipophilic phase, preferably selected from the group consisting of: Capmul MCM, Labrafil M-1944 CS, Miglyol-812 and a combination thereof, said lipophilic phase in an amount of from about 5% to about 35% by weight of the total composition; polyethylene glycol having a mean molecular weight of greater than about 300 but less than about 600 in an amount of from about 10% to about 40% by weight of the total composition; and a pharmaceutically acceptable surfactant, preferably selected from the group comprising: a polyoxyl castor oil, a polyoxyethylene glycerol triricinoleate, and a saturated polyglycolyzed caprylic-capric glyceride, in an amount from about 20 to about 60 percent by weight of the total composition. It is preferred that such composition further comprise a basic amine, preferably selected from the group comprising: a lower alkylamine, basic amino acid, or choline hydroxide, said basic amine preferably in an amount from about 0.1% to about 10% by weight of the total composition.

BRIEF DESCRIPTION OF THE DRAWINGS

The above description, as well as further objects, features and advantages of the present invention will be more fully understood with reference to the following detailed description when taken in conjunction with the accompanying drawings, wherein.

DETAILED DESCRIPTION OF THE INVENTION

Figure 1:
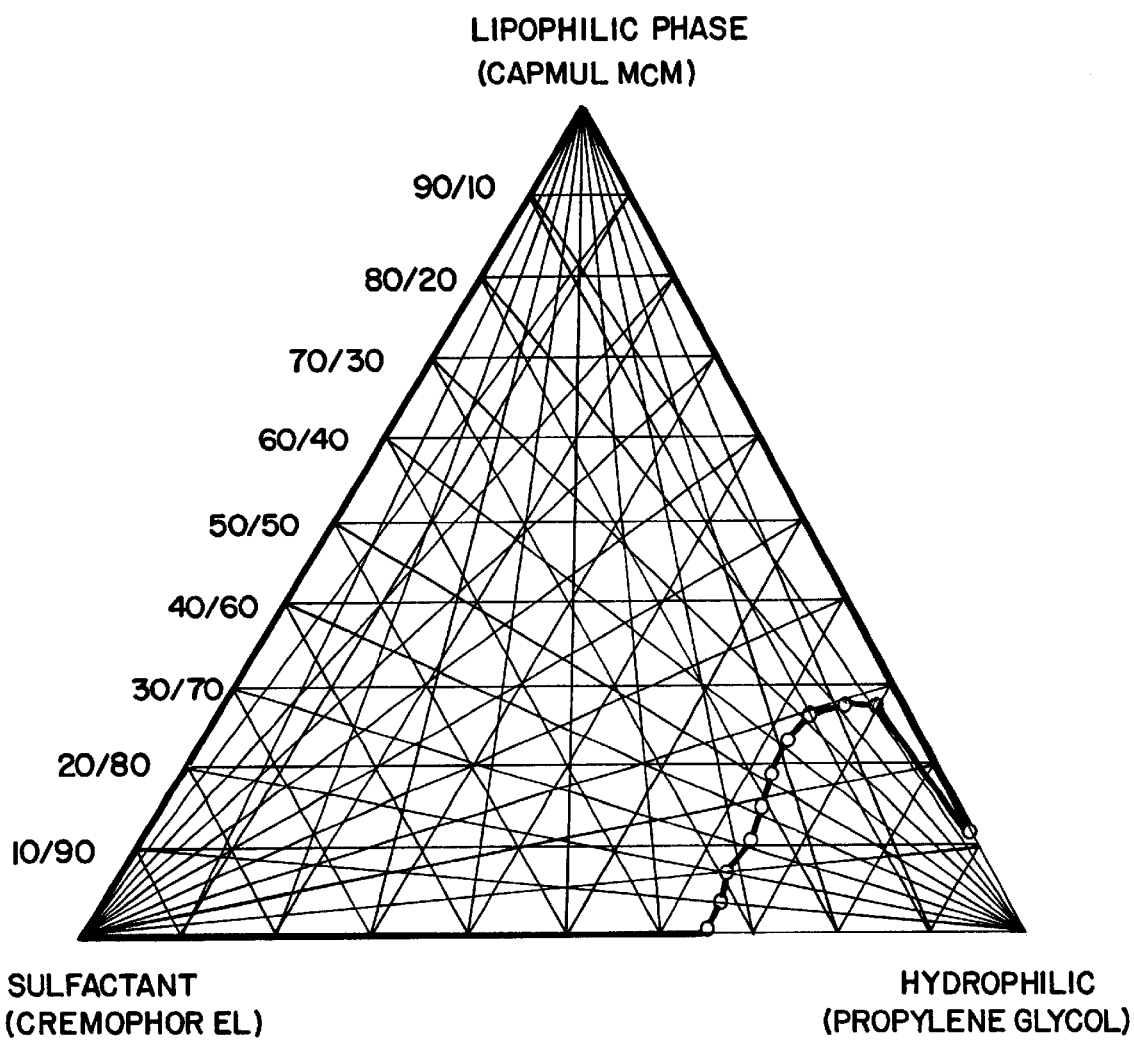
FIG. 1 is a phase diagram of a microemulsion comprising Cremophor EL as the surfactant, propylene glycol as the hydrophilic phase, and Capmul MCM as the lipophilic phase, at different concentration ratios with respect to one another.

The present invention overcomes many of the problems associated with the less than desirable stability and formulation characteristics of pyranone protease inhibitors. The present invention provides novel formulations of pyranone protease inhibitors that significantly improve the solubility and bioavailabilty of such protease inhibitors in oral dosage forms.

Dissolution performance is an important consideration in any oral formulation. Formulation, however, must also take into account the need for economically practicable methods to produce a wide range of oral potencies that are physiochemically stable. Further, components of any formulation must possess satisfactory processing properties. The present invention provides for the economical production and processing of physiochemically stable oral dosage forms of pyranone protease inhibitors having improved bioavailability.

Compounds of Formulas I, II, III, and IV of this application are disclosed and claimed in International Patent Application No. PCT/US95/05219 and may be prepared according to the procedures described in International Patent Application No. WO 95/30670, the disclosures of which are incorporated herein in their entirety by reference. By "pyranone protease inhibitor" is meant any compound defined by Formulas I, II, III and IV which inhibit retroviral protease.

The self-emulsifying formulation of the present invention refers to a composition comprising a pyranone protease inhibitor, a lipophilic phase, a hydrophilic phase preferably with polyethylene glycol, one or more pharmaceutically acceptable surfactants and a basic amine in the amount from 0.1% to about 10% by weight of total composition. By "self-emulsifying formulation" it is meant a concentrated composition capable of generating emulsions or microemulsions upon mixing with sufficient aqueous media. The emulsions or microemulsions generated from the present invention are solutions comprising a hydrophilic phase and lipophilic phase. Microemulsions are also characterized by their thermodynamic stability and small average droplet size, generally less than about 0.15 microns.

By "basic amine" is meant lower alkylamines such as, for example, ethanolamine, diethanolamine, triethanolamine, dimethylaminoethanol, tris(hydroxy-methyl)aminomethane or ethylenediamine; quaternary ammoniums such as, for example, choline hydroxide; basic amino acids such as, for example, arginine, lysine or guanidine. The preferred lower alkylamine is dimethylaminoethanol or tris(hydroxy-methyl)aminomethane.

By the term "pharmaceutically acceptable surfactant" is meant to include non-ionic surfactants, including Polyoxyl 40 hydrogenated castor oil sold under the trade name, among others, Cremophor RH40; Polyoxyl 35 castor oil sold under the trade name, among others, Cremophor EL or Cremophor EL-P (BASF Corp.); Polysorbates; Solutol HS-15; Tagat TO; Peglicol 6-oleate; Polyoxyethylene stearates; saturated polyglycolyzed caprylic-capric glycerides sold under the trade name, among others, Labrasol (Gattefosse, Westwood N.J.); saturated polyglycolyzed glycerides; or poloxamers, all of which are commercially available The preferred surfactant is Cremophor EL.

By "lipophilic component" or "lipophilic phase" is meant to include any number of components exhibiting lipid-like properties, and high solubility in lipids, and includes triglycerides of caprylic/capric acid, sold under the trade name, among others, of Captex 300 (Abitec, Columbus, Ohio.), trans-esterification products of kernel oil and PEG (or unsaturated polyglycolyzed glycerides obtained by partial alcoholyisis of apricot kernel oil consisting of glycerides and PEG esters), known under the trade name, among others, of Labrafil M 1944 CS (Gattefosse, Westwood, N.J.); mono- and di- glycerides of caprylic and capric acid in glycerol, known under the trade name, among others, as Capmul MCM (Abitec, Columbus, Ohio.); and fractionated oil (such as coconut oil) containing caprylic-capric acids triglycerides, known under the trade name, among others, as Miglyol 812.

By the term "monoglyceride" is meant a fatty acid ester of glycerol having structural formula $HOCH_2$—$CH(OH)$—$CH_2(O_2CR)$ or $HOCH_2$—$CH(O_2CR)$—$CH_2OH$, wherein R is a mono-saturated or di-saturated alkyl group having eight to ten carbon atoms. By the term "diglyceride" is meant a fatty acid ester of glycerol having structural formula $HOCH_2$—$CH(O_2CR)$ —$CH_2(O_2CR)$— or $(RCO_2)CH_2$—$CH(OH)$—$CH_2(O_2CR)$, wherein R is mono-saturated or di-saturated alkyl group having eight to ten carbon atoms. A mixture of diglyceride and monoglyceride may be prepared by mixing individual diglyceride and monoglyceride in appropriate relative proportion and/or by partial hydrolysis of triglyceride, or transesterifcation reaction of triglycerides, diglycerides with glycerol.

By polyethylene glycol or PEG is meant a polymer having the general formula $HOCH_2(CH_2)CH_2)_mCH_2OH$, where m represents the average number of oxyethylene groups. The number which follows PEG indicates the average molecular weight of the polymer. Commercially, PEG may be obtained from the Union Carbide Corp., among other sources.

In a particularly advantageous composition of the present invention with respect to the composition of Formula IV (tipranavir), there is provided a PEG-based self-emulsifying vehicle containing between about 10 percent to about 40 percent PEG 400 (more preferably about 15 percent to about 30 percent PEG 400), between about 20 percent to about 60 percent Cremophor EL (more preferably about 35 percent to about 50 percent Cremophor EL), between about 5 percent to about 35 percent Capmul MCM (more preferably between about 7 percent to about 15 percent Capmul MCM), and between about 0.1 percent to about 10 percent basic amine.

It has been noted that conventional self-emulsifying formulations of pyranone protease inhibitors comprising propylene glycol and/or alcohol stored for periods of time in soft gelatin capsules exhibit slower and less complete dispersion in aqueous medium, and an approximately 40 percent decrease in dissolution compared to comparable freshly made formulations. It has also been noted that the bioavailability of these drugs in humans is lower than that of a bulk solution of similar formulation that is filled into gelatin capsules immediately before administration. It was hypothesized that such effects could be attributable to solvent in the formulation migrating into the capsule.

Initial studies were undertaken to alter the gelatin formulation of the capsule to prevent migration of solvents from the emulsifying formulation into the capsule. Such attempts were not successful. Studies were then undertaken to determine if the propylene glycol and alcohol solvents used in conventional formulations could be replaced in whole or part with another solvent.

Microemulsion phase diagrams were constructed for systems containing various lipophilic phases, hydrophilic phases, and surfactants. After numerous studies it was determined that a number of pyranone protease inhibitors, including tipranavir, were soluble in polyethylene glycols within a defined average molecular weight range, and could be used to replace propylene glycol and ethanol found in conventional microemulsion formulations of such drugs.

FIG. 1 is a phase diagram of a microemulsion comprising Cremophor EL as the surfactant, Capmul MCM as the lipophilic phase and, as in conventional formulations of pyranone protease inhibitors, propylene glycol as the hydrophilic phase at different concentration ratios with respect to one another. As can be seen, such composition provides a stable microemulsion over a wide array of concentrations of each component. As propylene glycol is soluble in the capsule surrounding the formulation, however, the point defining the formulation in the phase diagram can vary considerably over time as more propylene glycol is removed from the emulsion. Consequently, the solubility of the drug in the formulation can change considerably over time.

Figure 2:
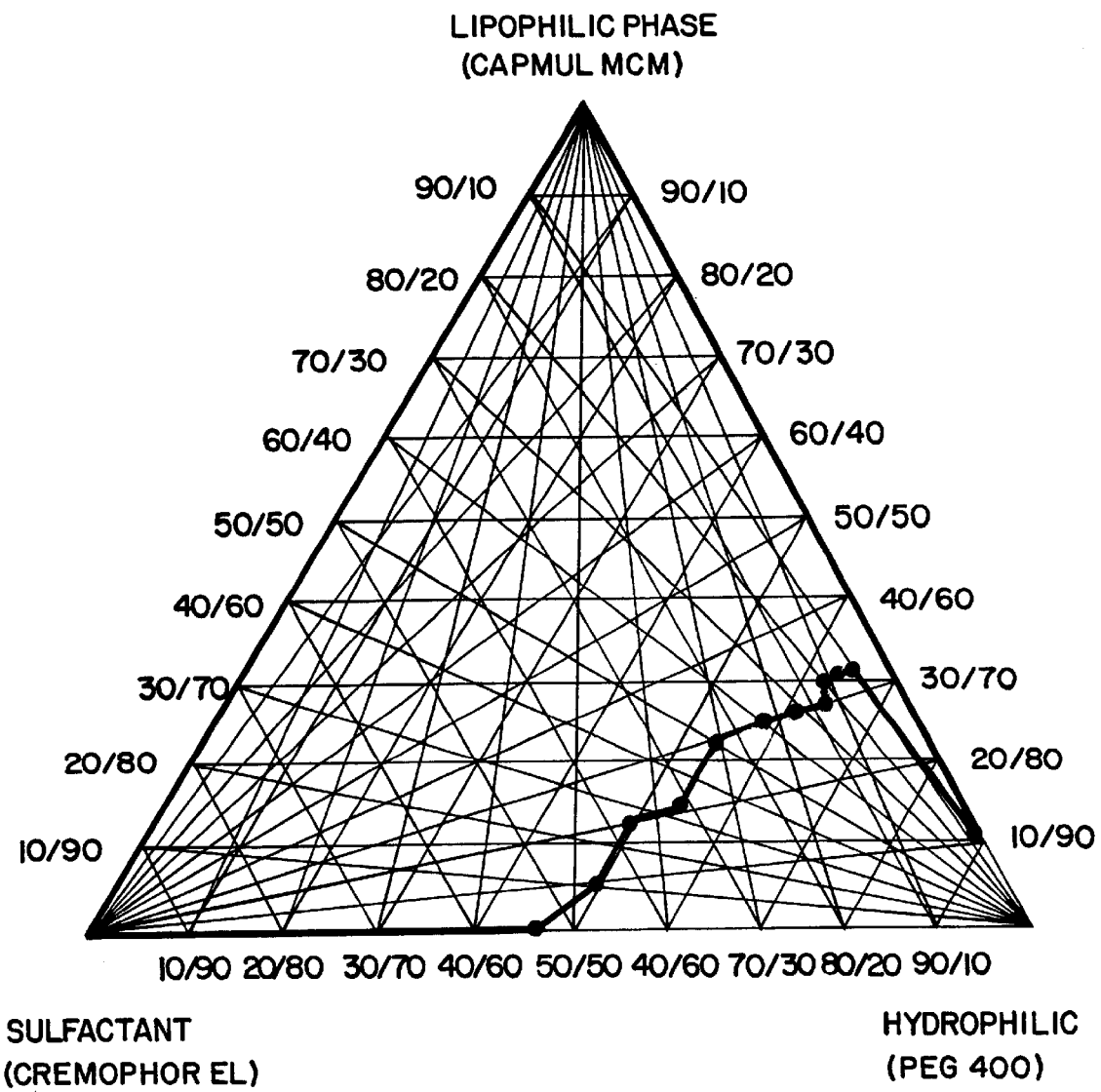
FIG. 2 is a phase diagram of a microemulsion comprising Cremophor EL as the surfactant, PEG 400 as the hydrophilic phase, and Capmul MCM as the lipophilic phase at different concentration ratios with respect to one another.

FIG. 2 is a phase diagram of a microemulsion comprising Cremophor EL as the surfactant, Capmul MCM as the lipophilic phase, and PEG-400 as the hydrophilic phase again at different concentration ratios with respect to one another. The phase diagram employing PEG-400 (rather than propylene glycol as in FIG. 1) can be characterized as similar to that of that seen in FIG. 1.

Figure 3:
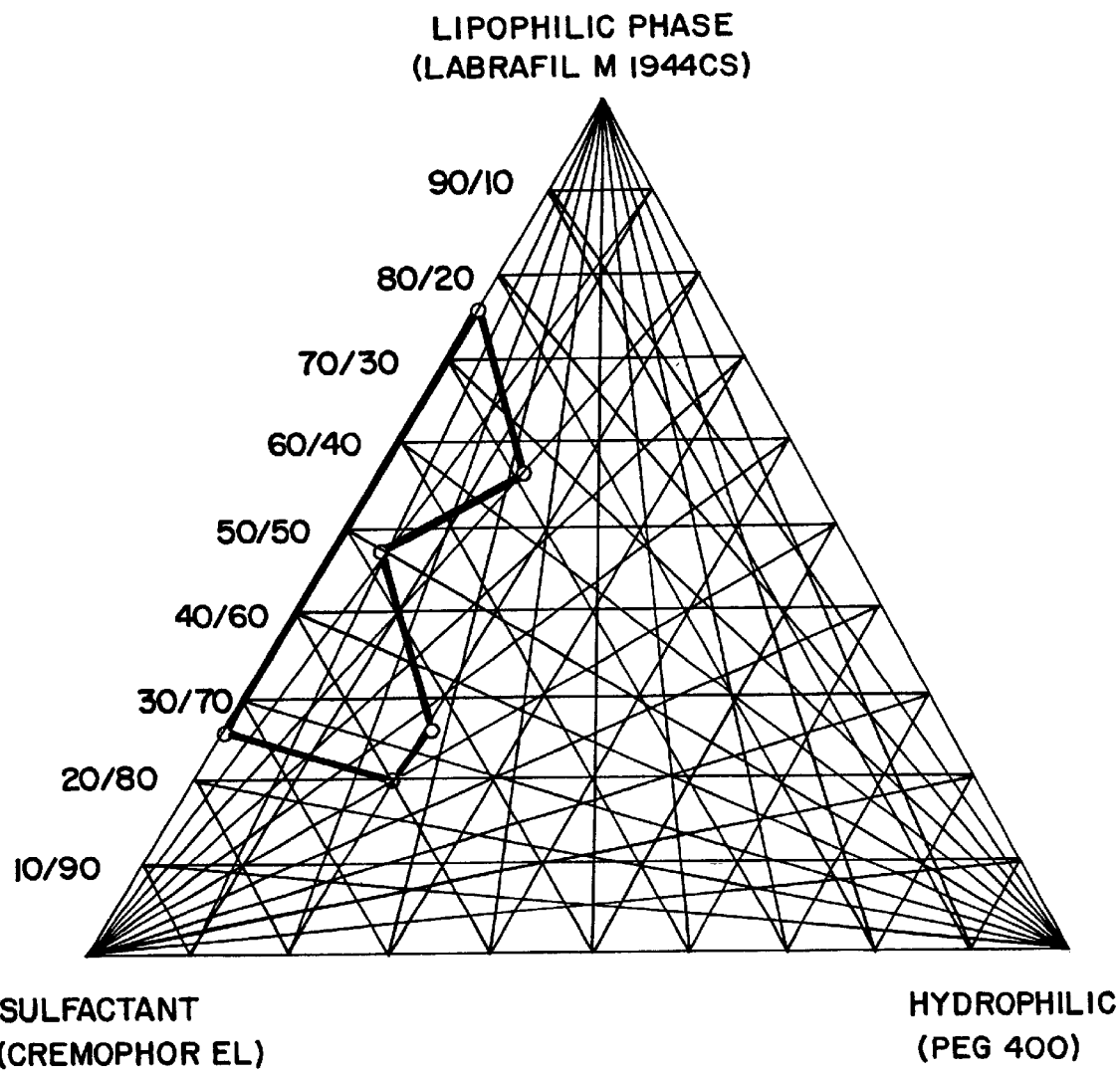
FIG. 3 is a phase diagram of a microemulsion comprising Cremophor EL as the surfactant, PEG 400 as the hydrophilic phase, and Labrafil M-1944 CS as the lipophilic phase at different concentration ratios with respect to one another.

Studies undertaken to determine the effect of the lipophilic phase on the phase stability of the microemulsion of FIG. 2, suggest that it is preferred that the lipophilic phase comprise a mixture of medium chain mono- and di-glycerides, such as found in Capmul MCM. FIG. 3 is a phase diagram of a microemulsion comprising Cremophor EL as the surfactant, PEG 400 as the hydrophilic phase, and Labrafil-M-1944 CS as the lipophilic phase at different concentration ratios with respect to one another. Labrafil-M-1944 is a trans-esterification product of kernel oil and PEG, that is, unsaturated polyglycolyzed glycerides obtained by partial hydrolysis of apricot kernel oil, consisting of glycerides and PEG esters. The stability of the microemulsion over a wide range of concentrations of components was found to be more limited than the microemulsion system of FIG. 2 which employed Capmul MCM as the lipophilic phase. Capmul MCM is a mono- and di-glyceride mixture of caprylic/capric acid in glycerol.

Figure 4:
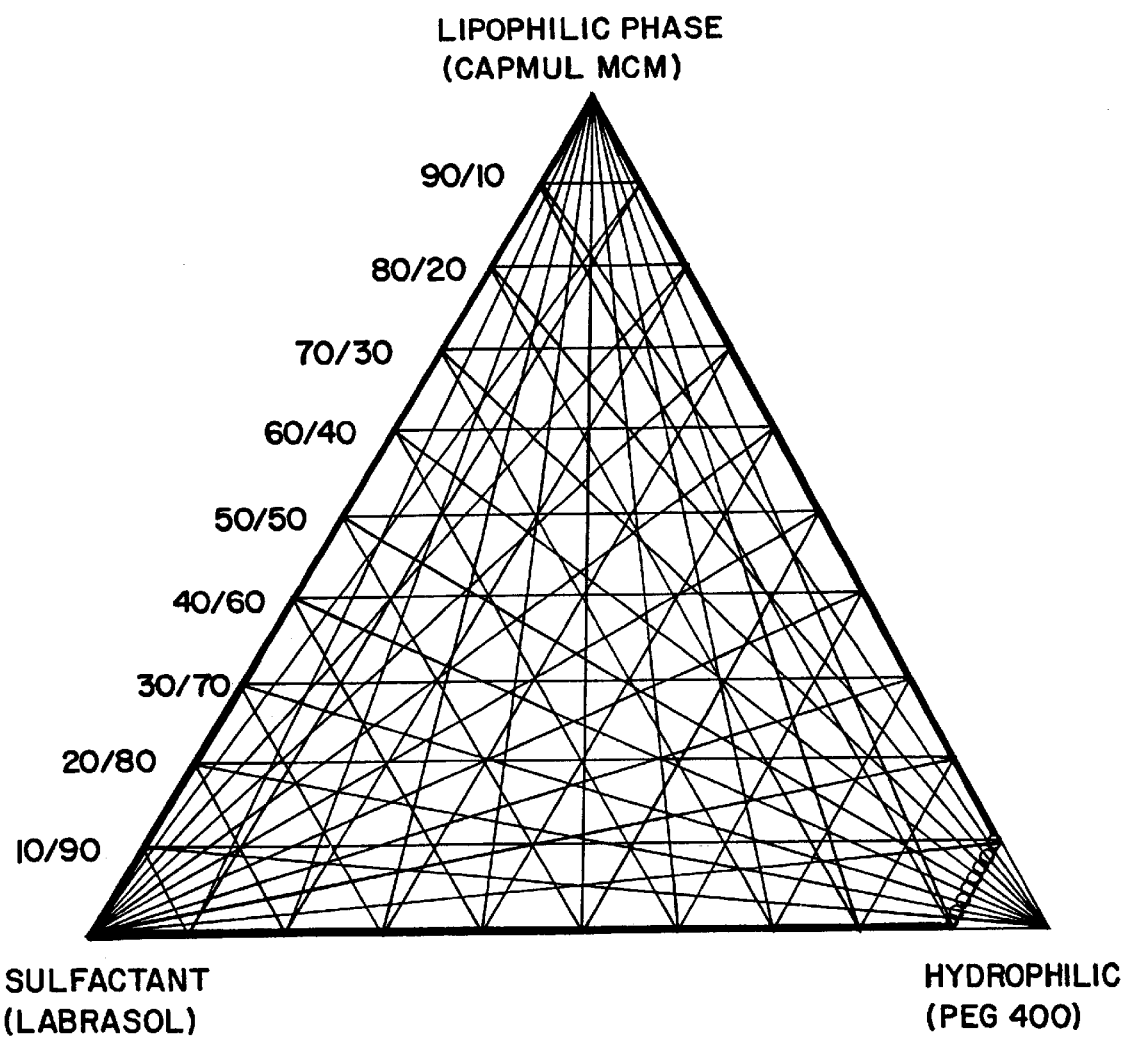
FIG. 4 is a phase diagram of a microemulsion comprising Labrasol as the surfactant, PEG 400 as the hydrophilic phase, and Capmul MCM as the lipophilic phase, at different concentration ratios with respect to one another.

Slight improvement in the stability of the microemulsion of FIG. 2 was found by employing Labrasol as the surfactant rather than Cremophor EL. FIG. 4 is a phase diagram of a microemulsion comprising Labrasol as the surfactant, PEG 400 as the hydrophilic phase, and Capmul MCM as the lipophilic phase, at different concentration ratios with respect to one another. While Labrasol provided improved stability, Labrasol suffers from the disadvantage that its long term safety for oral use in humans has not yet been demonstrated.

Figure 5:
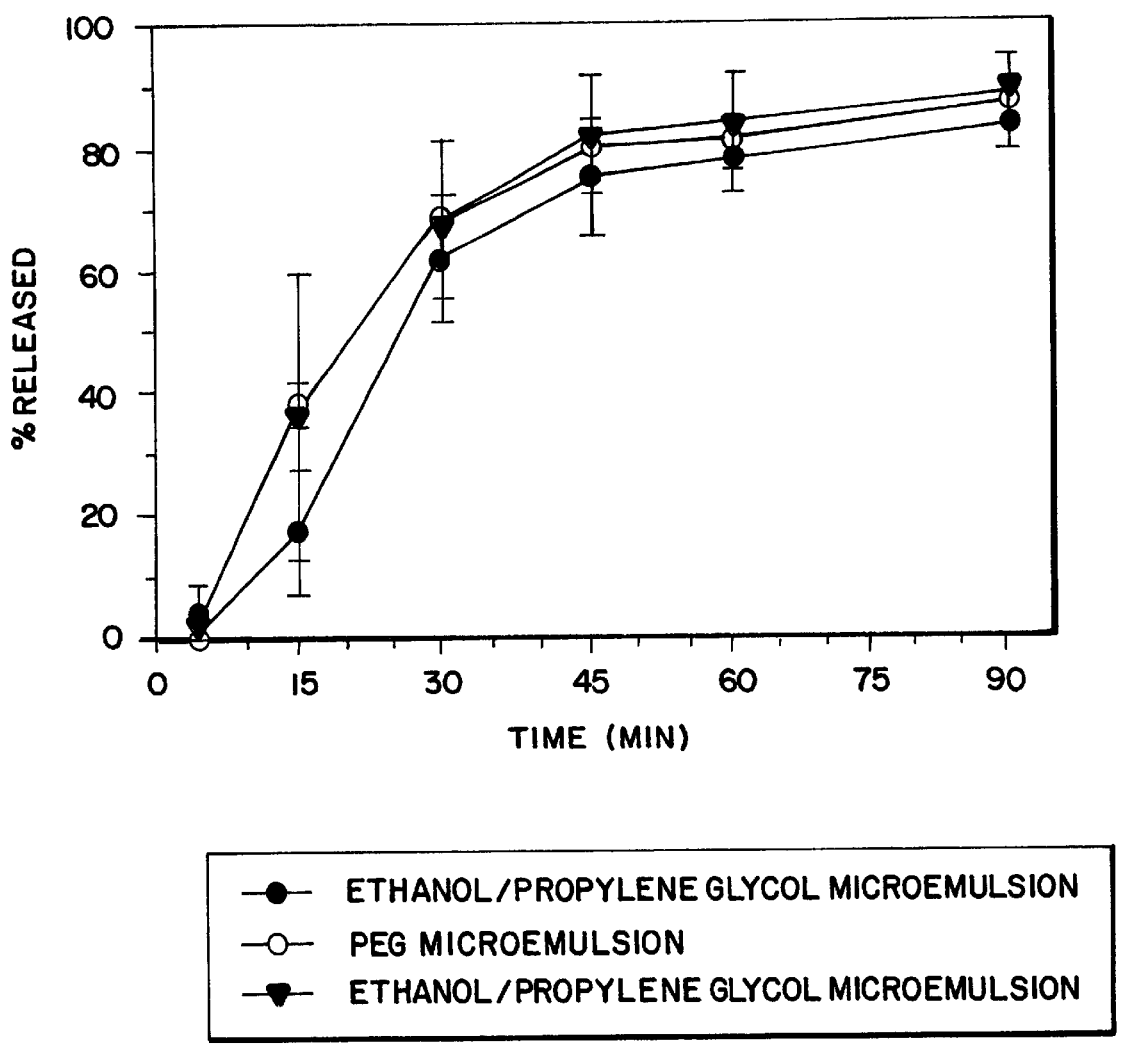
FIG. 5 is a graph of the in vitro dissolution of tipranavir from the two microemulsion formulations set forth in Table 1 and Table 2.

FIG. 5 is a graph of the in vitro dissolution of tipranavir from two self-emulsifying formulations set forth in Table 1 and Table 2. The formulation set forth in Table 2 differs from that in Table 1 in the replacement of the alcohol and propylene glycol with PEG 400.

TABLE 1

| Component | Amount | % w/w |
|---|---|---|
| Tipranavir | 250 | 25 |
| Alcohol | 100 | 10 |
| Propylene Glycol | 73 | 7.3 |
| Cremophor EL | 455 | 45.5 |
| Capmul MCM | 75 | 7.5 |
| Tromethamine USP | 15 | 1.5 |
| Purified Water USP | 30 | 3.0 |
| Propyl Gallate | 2 | 0.2 |
| Soft gelatin capsule | — | — |
| Total | 1000 | 100 |

TABLE 2

| Component | Amount | % w/w |
|---|---|---|
| Tipranavir | 250 | 25 |
| PEG 400 | 173 | 17.3 |
| Cremophor EL | 455 | 45.5 |
| Capmul MCM | 75 | 7.5 |
| Tromethamine USP | 15 | 1.5 |
| Purified Water USP | 30 | 3.0 |
| Propyl Gallate | 2 | 0.2 |
| Soft gelatin capsule | — | — |
| Total | 1000 | 100 |

In vitro dissolution of the formulation of Table 2 (using PEG 400 instead of alcohol and propylene glycol as hydrophilic solvent as used in the formulation of Table 1), was found to be nearly identical to that of the formulation of Table 1 when such formulation was freshly filled into the soft gelatin capsules. In vitro dissolution of the formulation of Table 2, on the other hand, was found to be substantially better over dissolution time than that of the Formulation of Table 1 when the formulation of Table 1 was refrigerated in the soft gelatin capsules at 4° C. for 14 months.

The self-emulsifying formulation of Table 2 was found to offer exceedingly good stability at room temperature as well as under refrigeration, whether stored in hydrophilic or lipophilic soft gel capsules kept in induction-sealed HDPE bottles.

Figure 6:
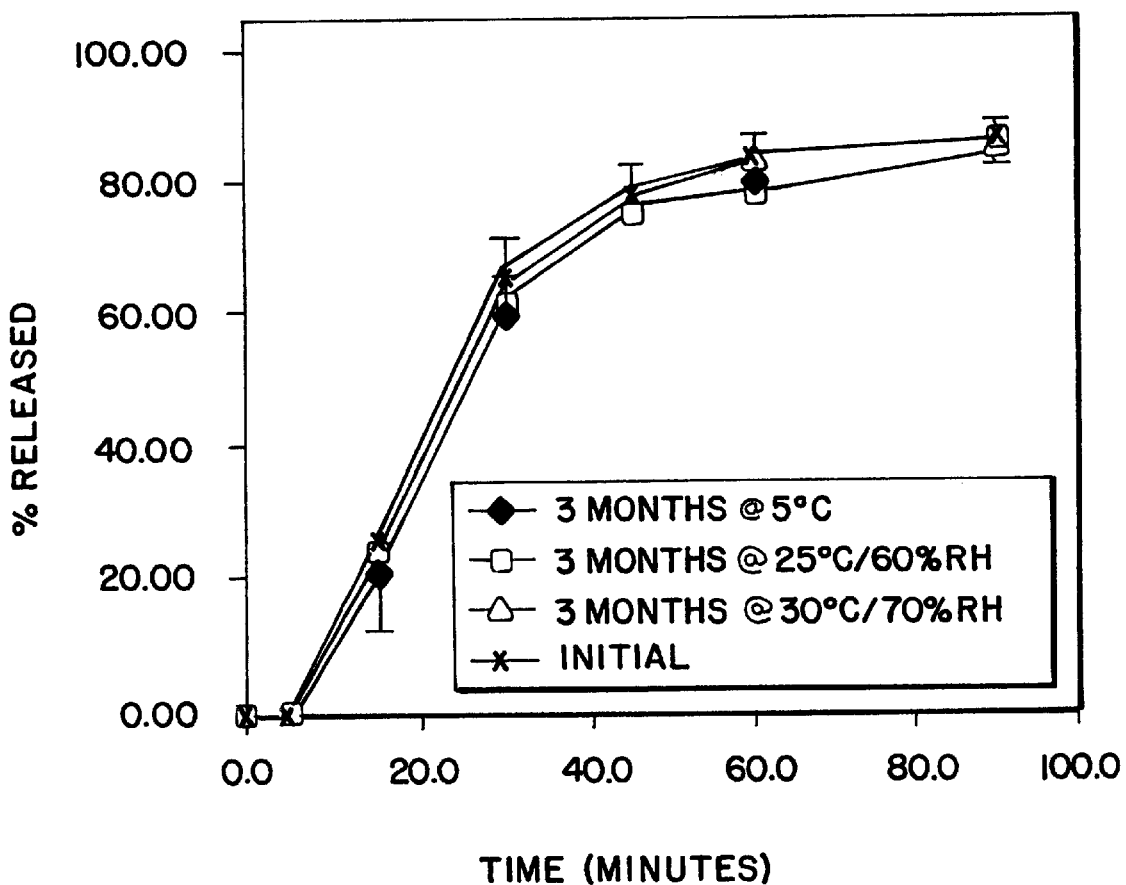
FIG. 6 is a graph of the in vitro dissolution of tipranavir from the self-emulsifying formulation as set forth in Table 2 encapsulated in a hydrophilic soft gel cap, after storing for 3 months, at different temperatures and/or relative humidities.

FIG. 6 is a graph of the in vitro dissolution of tipranavir from the formulation as set forth in Table 2 encapsulated in a hydrophilic soft gel capsule and stored in induction-sealed HDPE bottles, after storing for different periods of time at different temperatures and/or relative humidities. All three preparations depicted, those kept for 3 months at 5° C., those kept at room temperature (25° C.) for 3months at 60% relative humidity, and those kept at 30° C. for 3 months at 70% relative humidity, resulted in nearly identical dissolution profiles.

Figure 7:
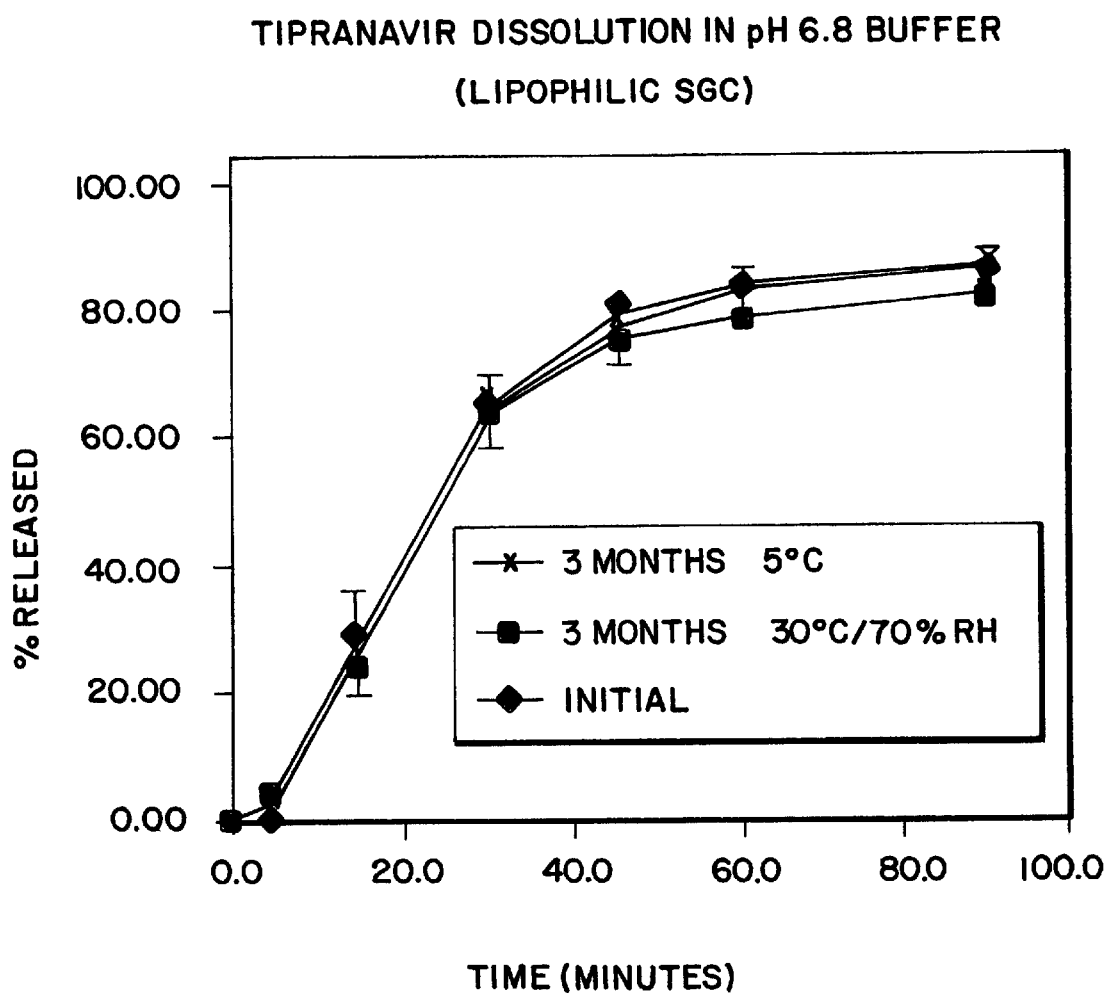
FIG. 7 is a graph of the in vitro dissolution of tipranavir from the self-emulsifying formulation set forth in Table 2 encapsulated in a lipophilic soft gel cap, after storing for 3 months, at different temperatures and/or relative humidities.

FIG. 7 is a graph of the in vitro dissolution of tipranavir from the formulation as set forth in Table 2 encapsulated in a lipophilic soft gel cap, after storing for different periods of time at different temperatures and/or relative humidities. Nearly identical patterns as seen with the formulation encapsulated in hydrophilic soft gel capsules were discerned. The formulation of Table 2 when stored in lipophilic soft gel capsules demonstrated remarkable stability in dissolution profile when stored in induction-5 sealed HDPE bottles for 3 months at 5° C. or 30° C. at a relative humidity of 70%.

EXAMPLE 1

Preparation of a PEG-Based Tipranavir SEDDS Formulation 455 mg of Cremophor EL, 75 mg of Capmul MCM, and 173 mg of PEG 400 were added to a mixing vessel and mixed (700 rpm) together while adding 2 mg of propyl gallate as an antioxidant. Mixing was continued until the solution was clear, then 15 mg of Tris (predissolved in water in a 1:2 ratio) was added. Mixing was continued at high speed (1600 rpm) as tipranavir (250mg) was added to the solution. When the tipranavir was completely dissolved, mixing was subsequently stopped and the solution allowed to stand for de-gassing.

EXAMPLE 2

Bioavailability of PEG-Based Tipranavir Self-Emulsifying Formulation

Male beagle dogs were used for the in vivo oral bioavailability study. A PEG-based tipranavir formulation as set forth in Table 2 was compared in dogs to the propylene glycol/ethanol formulation as set forth in Table 1 after encapsulation in soft gelatin capsules. The bioavailability of the two formulations is found to be statistically the same.

Further stability studies have been conducted with the formulation set forth in Table 2 in standard soft gelatin capsules. Such studies have shown that the formulation of the present invention presents less impurities and so appears to be more stable than the formulation set forth in Table 1 in standard soft gelatin capsules. Additionally, the soft gelatin capsules having the self-emulsifying formulation according to the present invention were not sticky at six months, 30° C. and 70% relative humidity.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety by reference.

What is claimed is:

1. A pharmaceutical composition substantially free of alcohol and propylene glycol comprising:

(a) a pyranone compound of Formula I as a pharmaceutically active agent,

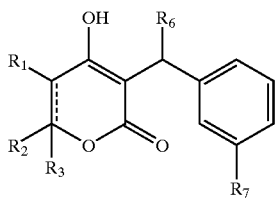

Formula I wherein $R_1$ is H—; $R_2$ is $C_3$–$C_5$ alkyl, phenyl-$(CH_2)_2$—, het-$SO_2NH$—$(CH_2)_2$—, cyclopropyl-$(CH_2)_2$—, F-phenyl-$(CH_2)_2$—, het-$SO_2NH$-phenyl-, or $F_3C$—$(CH_2)_2$—; or $R_1$ and $R_2$ taken together are a double bond; $R_3$ is $R_4$ —$(CH_2)_n$—$CH(R_5)$—, $H_3C$—$[O(CH_2)_2]_2$—$CH_2$—, $C_3$–$C_5$ alkyl, phenyl-$(CH_2)_2$—, het-$SO_2NH$—$(CH_2)_2$—, $(HOCH_2)_3$ C—NH—C(O)—NH—$(CH_2)_3$—, $(HO_2C)(H_2N)CH$—$(CH_2)_2$—C(O)—NH—$(CH_2)_3$—, piperazin-1-yl-C(O)—NH—$(CH_2)_3$, $HO_3S(CH_2)_2$—N($CH_3$)—C(O)—$(CH_2)_6$—C(O)—NH—$(CH_2)_3$—, cyclopropyl-$(CH_2)_2$—, F-phenyl-$(CH_2)_2$—, het-$SO_2$ NH-phenyl, or $F_3C$—$(CH_2)_2$—; n is 0, 1 or 2; $R_4$ is phenyl, het, cyclopropyl, $H_3C$—$[O(CH_2)_2]_2$—, het-$SO_2NH$—, Br—, $N_3$—, or $HO_3S(CH_2)_2$—N($CH_3$)—C(O)—$(CH_2)_6$—C(O)—NH—; $R_5$ is —$CH_2$—$CH_3$, or —$CH_2$-cyclopropyl; $R_6$ is cyclopropyl, $CH_3$—$CH_2$—, or t-butyl; $R_7$ is —$NR_8SO_2$-het, —$NR_8SO_2$-phenyl, optionally substituted with $R_9$,—$CH_2$—$SO_2$-phenyl, optionally substituted with $R_9$, or —$CH_2$—$SO_2$-het; $R_8$ is —H, or —$CH_3$; $R_9$ is —CN, —F, —OH, or —$NO_2$; wherein het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —C(O)$OC_2H_5$, —$CF_3$, —$NH_2$, or —C(O)—$NH_2$; or a pharmaceutically acceptable salt thereof;

(b) one or more pharmaceutically acceptable surfactants; and (c) a polyethylene glycol solvent having a mean molecular weight of greater than 300 but lower than 600.

2. A pharmaceutical composition substantially free of alcohol and propylene glycol comprising:

(a) a pyranone compound of Formula II or III as a pharmaceutically active agent,

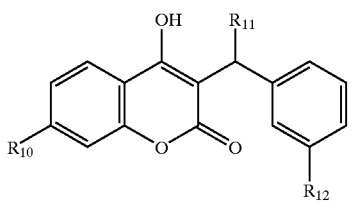

Formula II

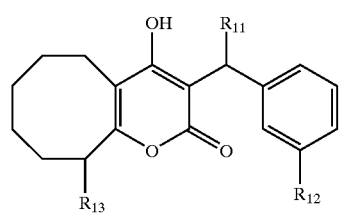

Formula III wherein $R_{10}$ is H—, $CH_3O$—, or $CH_3O$—$[(CH_2)_2O]_3$—; $R_{11}$ is cyclopropyl, or —$CH_2$—$CH(CH_3)_2$; $R_{12}$ is —$NR_{14}SO_2$-phenyl, optionally substituted with $R_{15}$,— $NR_{14}SO_2$-het, —$CH_2$—$SO_2$-phenyl, optionally substituted with $R_{15}$, or —$CH_2$—$SO_2$-het; $R_{13}$ is —H, —$(CH_2)_2$—$CH_3$, —$CH_2$-cycloproryl, or —$CH_2$-phenyl; $R_{14}$ is —H, or —$CH_3$; $R_{15}$ is —CN, —F, —$CH_3$, —COOH, or —OH; het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle; optionally substituted with one or two —$CH_3$, —CN, —C(O)$OC_2H_5$, or —OH; or a pharmaceutically acceptable salt thereof;

(b) one or more pharmaceutically acceptable surfactants; and (c) a polyethylene glycol solvent having a mean molecular weight of greater than 300 but lower than 600.

3. The pharmaceutical composition of claim 1 wherein the compound of Formula I is present in an amount from about 1% to about 40% by weight of the total composition.

4. The pharmaceutical composition of claim 2 wherein the compound of Formula II is present in an amount from about 1% to about 40% by weight of the total composition.

5. The pharmaceutical composition of claim 2 wherein the compound of Formula III is present in an amount of from about 1% to about 40% by weight of the total composition.

6. The pharmaceutical composition of claim 1 further comprising a basic amine in an amount from about 0.1% to about 10% by weight of the total composition.

7. The pharmaceutical composition of claim 2 further comprising a basic amine in an amount from about 0.1% to about 10% by weight of the total composition.

8. The pharmaceutical composition of claim 6 wherein the basic amine is a lower alkylamine, basic amino acid or choline hydroxide.

9. The pharmaceutical composition of claim 7 wherein the basic amine is a lower alkylamine, basic amino acid or choline hydroxide.

10. The pharmaceutical composition of claim 8 wherein the lower alkylamine is selected from the group consisting of: ethanolamine, diethanolamine, triethanolamine, ethylenediamine, dimethylaminoethanol or tris (hydroxymethyl) aminomethane.

11. The pharmaceutical composition of claim 9 wherein the lower alkylamine is selected from the group consisting of: ethanolamine, diethanolamine, triethanolamine, ethylenediamine, dimethylaminoethanol or tris (hydroxymethyl) aminomethane.

12. The pharmaceutical composition of claim 1 further comprising a mixture of diglyceride and monoglycerides in an amount from about 5% to about 35% by weight of the total composition.

13. The pharmaceutical composition of claim 2 further comprising a mixture of diglyceride and monoglycerides in an amount from about 5% to about 35% by weight of the total composition.

14. The pharmaceutical composition of claim 12 wherein the diglycerides and monoglycerides are medium chain in length.

15. The pharmaceutical composition of claim 13 wherein the diglycerides and monoglycerides are medium chain in length.

16. The pharmaceutical composition of claim 12 wherein the mixture of diglyceride and monoglycerides is Capmul MCM.

17. The pharmaceutical composition of claim 13 wherein the mixture of diglyceride and monoglycerides is Capmul MCM.

18. The pharmaceutical composition of claim 12 wherein the diglyceride and monoglyceride are mono- or di-saturated fatty acid esters of glycerol having eight to ten carbon chain length.

19. The pharmaceutical composition of claim 13 wherein the diglyceride and monoglyceride are mono- or di-saturated fatty acid esters of glycerol having eight to ten carbon chain length.

20. The pharmaceutical composition of claim 1 wherein the pyranone compound of Formula I is a compound of Formula IV:

Formula IV

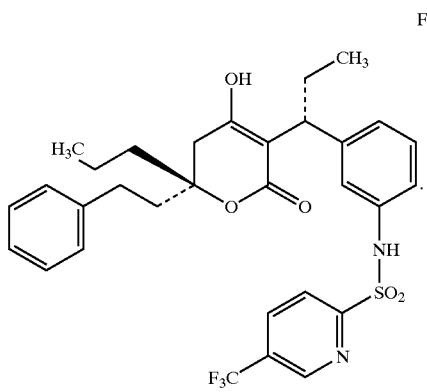

21. The pharmaceutical composition of claim 1 wherein the polyethylene glycol is in an amount of from about 10% to about 40% by weight of the total composition.

22. The pharmaceutical composition of claim 21 wherein the polyethylene glycol has an average molecular weight of about 400.

23. The pharmaceutical composition of claim 2 wherein the polyethylene glycol is in an amount of from about 10% to about 40% by weight of the total composition.

24. The pharmaceutical composition of claim 23 wherein the polyethylene glycol has an average molecular weight of about 400.

25. The pharmaceutical composition of claim 1 wherein the surfactant comprises from about 20% to about 60% by weight of the total composition.

26. The pharmaceutical composition of claim 2 wherein the surfactant comprises from about 20% to about 60% by weight of the total composition.

27. The pharmaceutical composition of claim 25 wherein the surfactant is Polyoxyl 40 hydrogenated castor oil, Polyoxyl 35 castor oil, Solutol HS-15, Tagat TO, Peglicol 6-oleate, Polyoxyethylene stearates, Poloxamers, Polysorbates, or Saturated Polyglycolyzed Glycerides.

28. The pharmaceutical composition of claim 26 wherein the surfactant is Polyoxyl 40 hydrogenated castor oil, Polyoxyl 35 castor oil, Solutol HS-15, Tagat TO, Peglicol 6-oleate, polyoxyethylene stearates, poloxamers, polysorbates, or saturated polyglycolyzed glycerides.

29. The pharmaceutical composition of claim 27 wherein the Polyoxyl 35 hydrogenated castor oil is Cremophor EL, or Cremophor EL-P.

30. The pharmaceutical composition of claim 28 wherein the Polyoxyl 35 hydrogenated castor oil is Cremophor EL, or Cremophor EL-P.

31. A substantially alcohol and propylene glycol free pharmaceutical pharmaceutical composition comprising:

(a) a pyranone compound of Formula IV

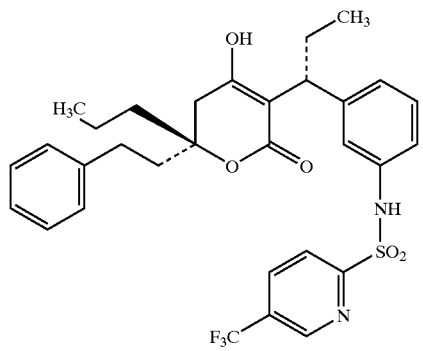

in an amount from about 1% to about 40% by weight of the total composition;

(b) a lipophilic phase comprising from about 5% to about 35% by weight of the total composition;

(c) polyethylene glycol having a mean molecular weight of greater than about 300 but less than about 600 in an amount from about 10% to about 40% by weight of the total composition;

(d) a surfactant selected from the group comprising: a polyoxyl castor oil, a polyoxyethylene glycerol triricinoleate, and a saturated polyglycolyzed caprylic-capric glyceride, in an amount from about 20 to about 60 percent by weight of the total composition; and (e) a basic amine selected from the group comprising: a lower alkylamine, basic amino acid, or choline hydroxide, said basic amine in an amount from about 0.1% to about 10% by weight of the total composition.

32. The pharmaceutical composition of claim 31 wherein the lipophilic phase comprises a mixture of diglycerides and monoglycerides.

33. The pharmaceutical composition of claim 31 wherein the lipophilic phase comprises a mixture of medium chain diglycerides and monoglycerides.

34. A substantially alcohol and propylene glycol free pharmaceutical composition comprising:

(a) a pyranone compound of Formula IV

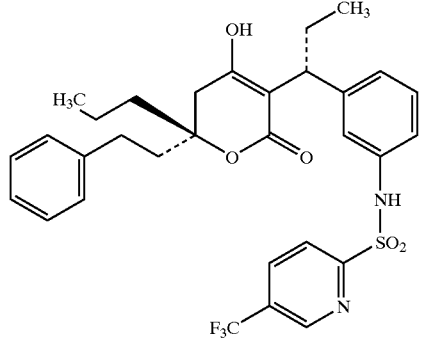

in an amount from about 1% to about 40% by weight of the total composition;

(b) a lipophilic phase selected from the group consisting of: Capmul MCM, Labrafil M-1944 CS and Myglol-812 and a combination thereof, said lipophilic phase in an amount from about 5% to about 35% by weight of the total composition;

(c) polyethylene glycol having a mean molecular weight of greater than about 300 but less than about 600 in an amount from about 10% to about 40% by weight of the total composition;

(d) a surfactant selected from the group comprising: a polyoxyl castor oil, a polyoxyethylene glycerol triricinoleate, and a saturated polyglycolyzed caprylic-capric glyceride, in an amount from about 20% to about 60% by weight of the total composition.

35. The composition of claim 34 further comprising a basic amine selected from the group comprising: a lower alkylamine, basic amino acid, or choline hydroxide, said basic amine in an amount from about 0.1% to about 10% by weight of the total composition.

36. The composition of claim 34 which is in a form of a liquid which can be encapsulated in soft elastic capsules.

37. The composition of claim 34 which is in a form of a liquid which can be encapsulated in hard gelatin or non-gelatin capsules.

* * * * *